(12) United States Patent
Arbuck

(10) Patent No.: US 10,543,093 B2
(45) Date of Patent: Jan. 28, 2020

(54) METHODS AND TOOLS FOR TREATING BONE PAIN

(71) Applicant: Dmitry Arbuck, Fishers, IN (US)

(72) Inventor: Dmitry Arbuck, Fishers, IN (US)

( * ) Notice: Subject to any disclaimer, the term of this patent is extended or adjusted under 35 U.S.C. 154(b) by 168 days.

(21) Appl. No.: 15/603,721

(22) Filed: May 24, 2017

(65) Prior Publication Data

US 2018/0000593 A1 Jan. 4, 2018

Related U.S. Application Data

(60) Provisional application No. 62/341,849, filed on May 26, 2016, provisional application No. 62/411,962, filed on Oct. 24, 2016.

(51) Int. Cl.
| | |
|---|---|
| *A61M 1/00* | (2006.01) |
| *A61F 2/30* | (2006.01) |
| *A61B 17/34* | (2006.01) |
| *A61M 5/142* | (2006.01) |
| *A61M 27/00* | (2006.01) |
| *A61B 17/00* | (2006.01) |
| *A61B 18/00* | (2006.01) |
| *A61M 5/158* | (2006.01) |

(52) U.S. Cl.
CPC ...... *A61F 2/30742* (2013.01); *A61B 17/3472* (2013.01); *A61M 5/142* (2013.01); *A61M 27/002* (2013.01); *A61B 2017/003* (2013.01); *A61B 2018/00011* (2013.01); *A61M 5/158* (2013.01)

(58) Field of Classification Search
CPC ...... A61B 17/3472; A61B 2018/00011; A61B 17/1655; A61B 2017/0073; A61B 2017/3492; A61M 27/002; A61M 5/158
See application file for complete search history.

(56) References Cited

U.S. PATENT DOCUMENTS

| | | | | |
|---|---|---|---|---|
| 6,122,549 A | * | 9/2000 | Sharkey | A61M 25/0133 606/27 |
| 9,775,627 B2 | * | 10/2017 | Patel | A61B 17/1671 |

* cited by examiner

*Primary Examiner* — Rebecca E Eisenberg
(74) *Attorney, Agent, or Firm* — Hartman Global IP Law; Gary M. Hartman; Domenica N. S. Hartman

(57) ABSTRACT

Methods and tools capable of treating diffuse or localized pain attributable to fluid accumulation within a bone. Such methods may utilize an instrument that includes a pilot adapted to penetrate soft tissue between the bone and the skin of a living being. The pilot is used in combination with a penetration tool to penetrate the bone, penetrate into the cortex of the bone, and form a seal against the surface of the bone, and after which fluid is removed from within the bone. Alternatively, the method may utilized a penetration tool equipped with a stopper bar to limit penetration to the periosteum of the bone, and/or may be implanted and connected to an implanted pump.

19 Claims, 11 Drawing Sheets

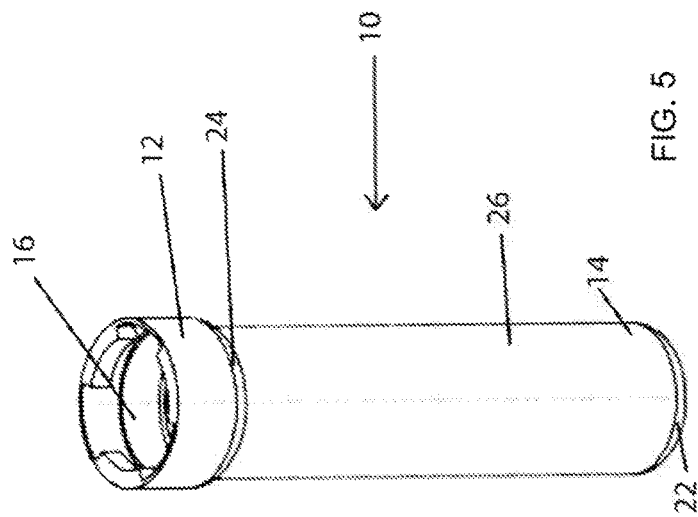
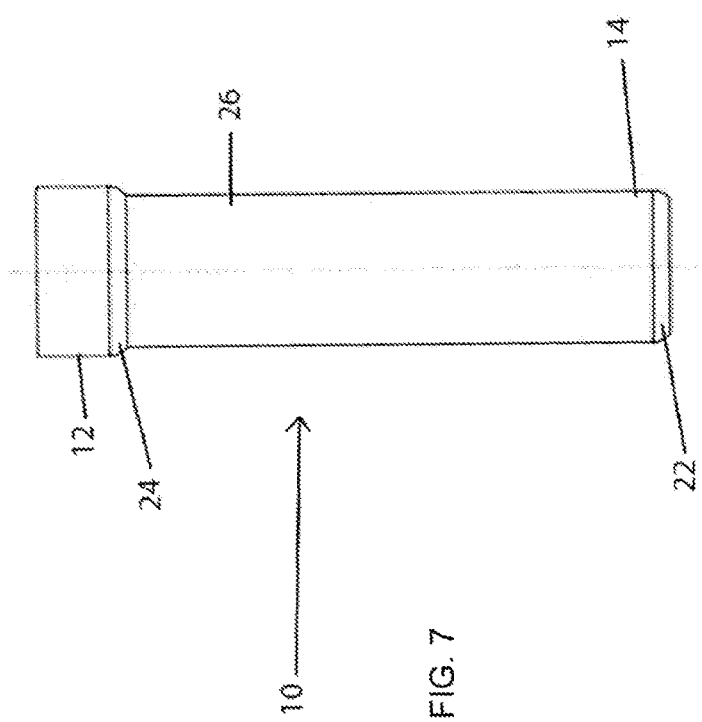
FIG. 5
FIG. 6
FIG. 7

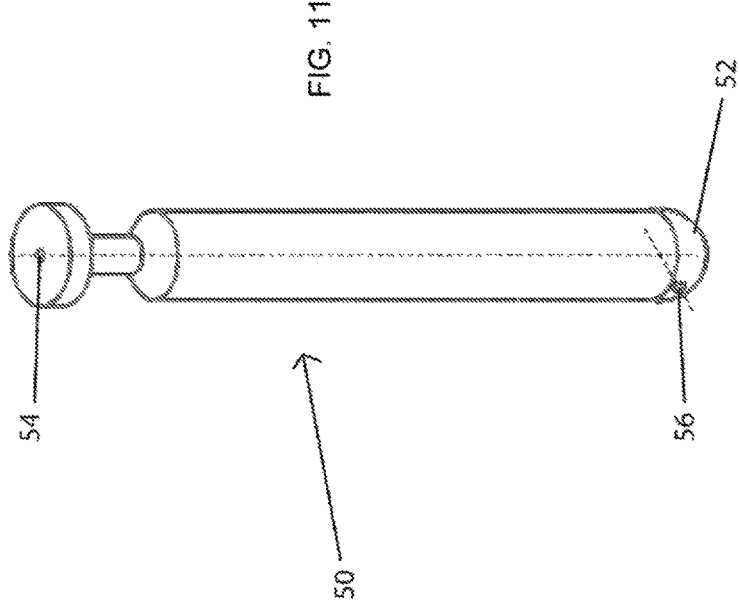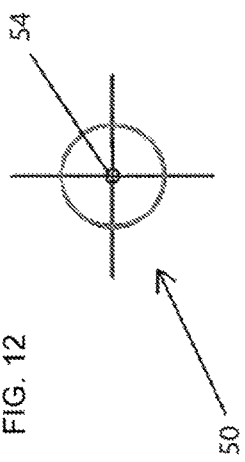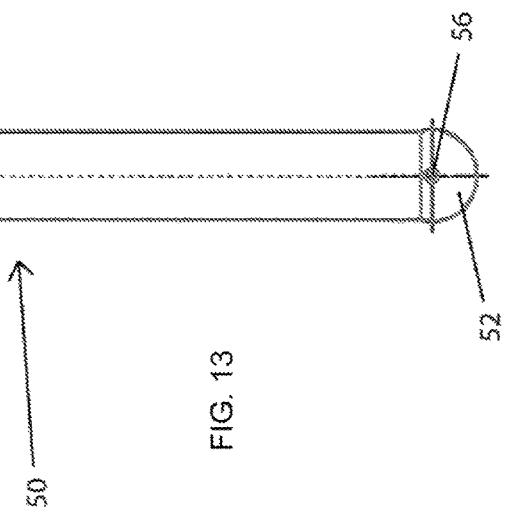

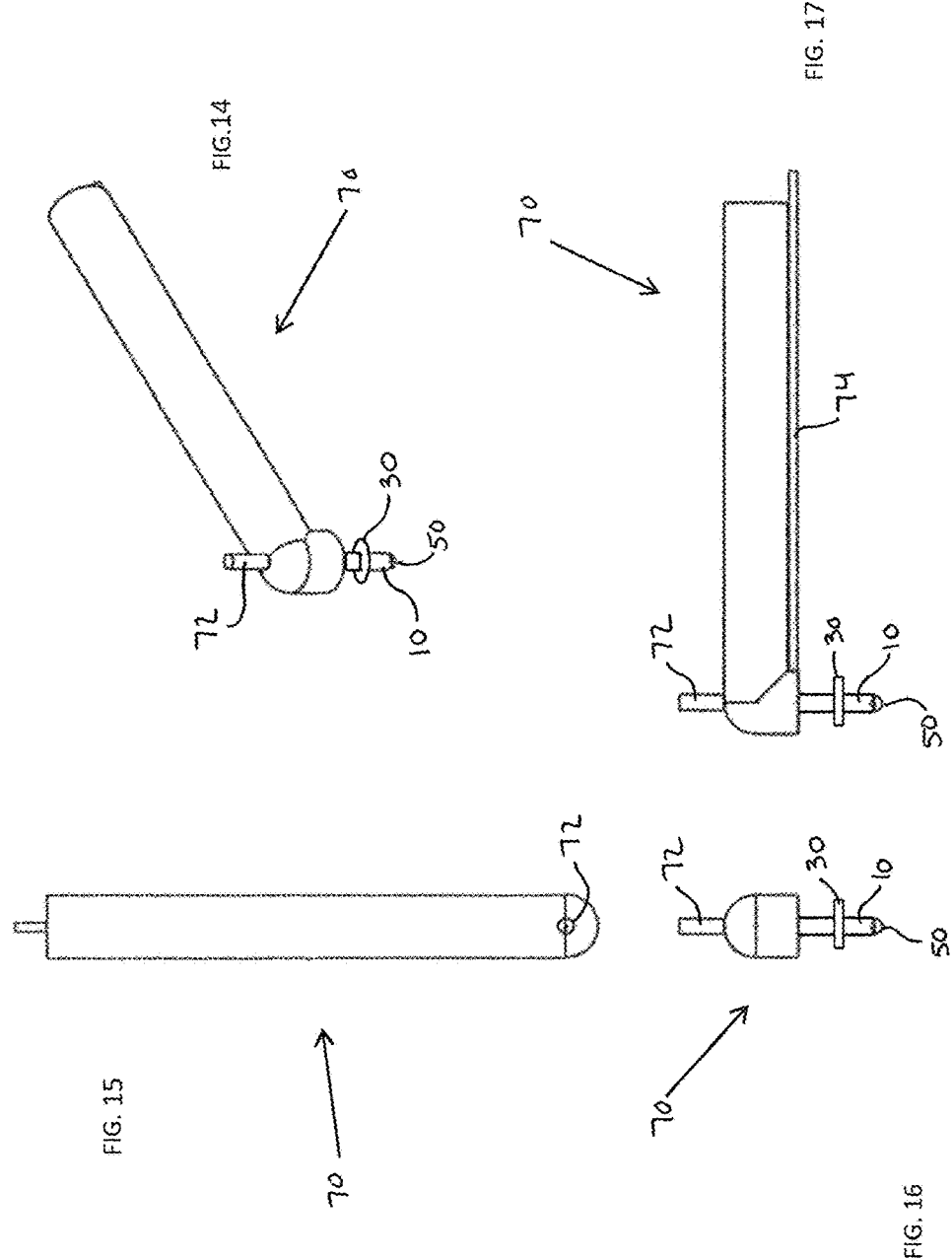

METHODS AND TOOLS FOR TREATING BONE PAIN

CROSS REFERENCE TO RELATED APPLICATIONS

This application claims the benefit of U.S. Provisional Application Nos. 62/341,849 filed May 26, 2016, and 62/411,962 filed Oct. 24, 2016. The contents of these prior patent applications are incorporated herein by reference.

BACKGROUND OF THE INVENTION

The present invention generally relates to methods and tools relating to treating pain, and particularly to reducing or eliminating a diffuse pain that is attributable to intraosseous pressure within a bone.

Individuals with medical conditions often suffer from pain. In many cases, the etiology of the pain is not clear. A common and well understood pain category is bone pain resulting from a variety of diseases such as trauma, trophic changes, and neoplasms. However, many chronic bone pain problems do not have clearly identifiable structural changes and hence are difficult to explain. Currently, such pain, without a readily attributable cause, is judged to be neuropathic in nature. In many such cases, medication treatment is heavily used if the nervous system is judged responsible and no peripheral causes are obvious. Further, surgical or interventional treatments are performed if obvious anatomical changes are found.

A large number of chronic pain conditions have possible explanation in subtle changes within the bones themselves. A "bone-pain generator" may be located in various bones, particularly the skull, pelvis, ribs, and vertebra, as well as facial and long bones. Increase in intraosseous pressure (i.e., pressure within a bone) due to chronic mechanical or metabolic influences can cause vague and diffuse pain symptoms that are not amenable to conventional surgical, interventional, or medication treatments. In the context of this disclosure, "diffuse pain" means pain whose source cannot be precisely pinpointed and is sensed over a general area, for example, overlying a locality where bone edema is present.

Thus there exists an unmet need for methods and tools that can mitigate bone pain, especially pain that is not amenable to hitherto known surgical, interventional or medication treatments due to being generated by a process that may be difficult to identify.

BRIEF DESCRIPTION OF THE INVENTION

The present invention provides methods and tools capable of treating bone pain in living beings.

According to one aspect of the invention, an instrument is provided for treating pain through decompression of a fluid (defined herein as a liquid, a vapor/gas, or combination thereof) within a bone of a living being. The instrument includes a pilot adapted to penetrate soft tissue between the bone and the skin of the living being. The pilot has a first opening at a first end thereof, a second opening at an oppositely-disposed second end thereof, an internal passage therebetween adapted for guiding a penetration tool, and a bevel at the second end. The bevel circumscribes the second opening and is configured to seal against a surface of the bone. The instrument further includes an anchor adapted for securing the pilot to the skin after the second end of the pilot has penetrated the skin and soft tissue, at least one penetration means sized to be inserted into the internal passage of the pilot and protrude through the second opening of the pilot, irrigation means for removing an irrigation fluid and bone debris created by drilling the bone with the penetration means, and suction means for removing the fluid from within the bone.

According to another aspect of the invention, a method is provided for treating pain through decompression of a fluid within a bone of a living being. The method includes identifying the bone of the living being as being associated with pain, using one or more tools to penetrate soft tissue between the bone and the skin of the living being, penetrate the bone of the living being, penetrate into the cortex of the bone, and form a seal against a surface of the bone, and removing the fluid from within the bone, wherein the fluid comprises a vapor.

According to yet another aspect of the invention, a method is provided that utilizes an instrument to treat pain through decompression of a fluid within a bone of a living being. The instrument includes a pilot having a first opening at a first end thereof, a second opening at an oppositely-disposed end thereof, an internal passage therebetween, and a bevel at the second end. The method includes placing the pilot on a surface of the skin of the living being at a location overlying a pain location of the bone, using a first penetration tool within the internal passage of the pilot and protruding through the second opening thereof to cause the pilot to penetrate soft tissue between the bone and the skin of the living being, securing the pilot to the skin after the second end of the pilot has penetrated the skin and soft tissue, using a second penetration tool within the internal passage of the pilot and protruding through the second opening thereof to cause the pilot to penetrate the bone of the living being, penetrate into the cortex of the bone, and seal the bevel at the second end of the pilot against a surface of the bone, removing the second penetration tool from the pilot, and then removing the fluid from within the bone.

Technical effects of the methods and tools described above preferably include the ability to mitigate pain by relieving intraosseous pressure attributable to low-volume fluid accumulation within a bone. The methods and tools are especially intended to be capable of reducing or eliminating diffuse pain symptoms that may not be treated by or respond to conventional surgical, interventional, or medication treatments.

Other aspects and advantages of this invention will be better appreciated from the following detailed description.

BRIEF DESCRIPTION OF DRAWINGS

FIGS. 5 through 7 schematically represent, respectively, perspective, top, and side views of a pilot capable of use in a nonlimiting pain treatment method of this disclosure.

FIGS. 11 through 13 schematically represent, respectively, perspective, top, and side views of a drill bit capable of use in a nonlimiting pain treatment method of this disclosure and shows irrigation entry and exit openings of the drill bit.

FIGS. 14 through 17 schematically represent, respectively, perspective, top, end, and side views an embodiment of an instrument comprising the pilot, anchor, and drill bit of FIGS. 5 through 13 and capable of use in a nonlimiting pain treatment method of this disclosure.

DETAILED DESCRIPTION OF THE INVENTION

Figure 1:
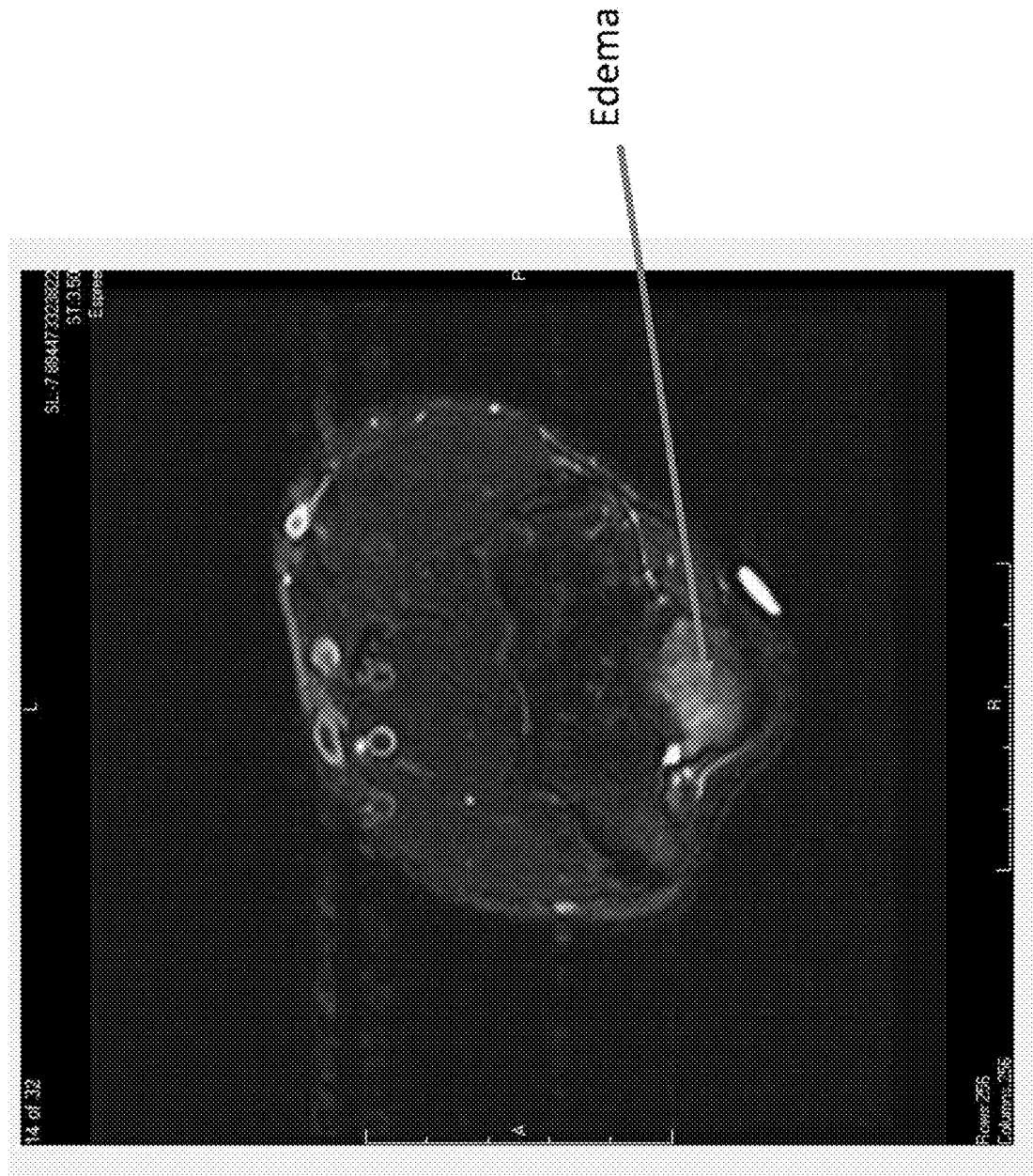
FIGS. 1 and 2 show X-ray images of the olecranon of the elbow of a young athlete showing edema due to a stress reaction.

For the purposes of promoting an understanding of the principles of the disclosure, reference will now be made to the embodiments illustrated in the drawings and specific language will be used to describe the same. The drawings are not to scale and therefore should not to be construed as limiting.

Intraosseous pressure due to various degrees of intraosseous edema and fluid (vapor) pressure can result in the sensation of pain. Intraosseous pressure and the resulting sensation of pain may vary from bone structure to bone structure and may not be fully appreciated by imaging devices, i.e., the images may not reveal or indicate the cause of the pain. Even low-grade edema in enclosed places (such as the skull, sternum, transverse or spinous processes of vertebras, ribs, hand, ankle bones, etc.) may cause pain.

This disclosure generally relates to methods and tools capable of treating pain in individuals, and particularly to reducing or eliminating a diffuse pain that is attributable to intraosseous pressure within a bone. These methods and tools provide for the decompression of intraosseous pressure and may be employed by physicians and other medical caregivers to reduce pain experienced by essentially any living being that has a skeleton typical of vertebrates. Decompression in this context means reducing the intraosseous pressure by removing a fluid (liquid and/or vapor/gas) from the bone. Such decompression is capable of normalizing the bone environment, stopping nociception, and decreasing if not eliminating the sensation of pain. The actual amount (volume) of accumulated fluid and numerical value of intraosseous pressure elevation sufficient for pain induction will vary from bone to bone and also from individual to individual.

Figure 2:
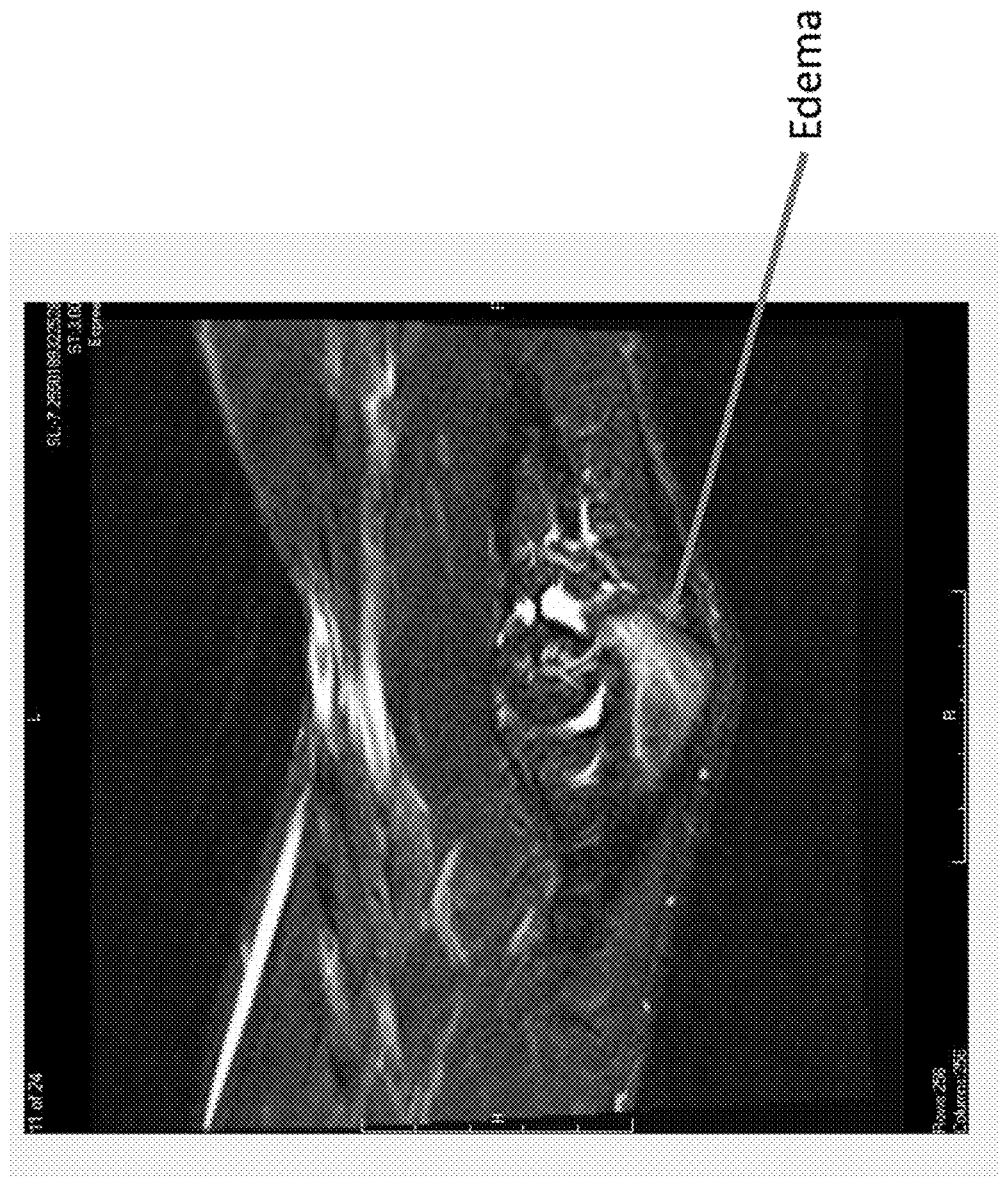

Though it is common practice to remove fluids from various organs (pleura, peritoneum, joint spaces, etc.) to mitigate pain caused by fluid accumulation, the amount of fluid removed is typically relatively large, ranging from a few milliliters to a few liters. On the other hand, the accumulation of a fluid (liquid or gas/vapor) within bony structures may be so small that it might be more particularly described as a gas or vapor. FIGS. 1 and 2 are images of the olecranon of an elbow of a young athlete showing relatively large intraosseous edema that was a stress reaction to trauma. FIGS. 1 and 2 are axial and sagittal images, respectively, of the olecranon. The white areas in the images indicate edema due to fluid accumulation and are labeled as such in FIGS. 1 and 2.

Unlike the intraosseous edema evident in FIGS. 1 and 2, which is a known physiological part of trauma, edema associated with other physiological conditions, for example, inflammation or immune-endocrine-metabolic tissue injury, ordinarily do not cause large accumulations of fluid, and as a result the volume of accumulated fluids may be measured in microliters (e.g., less than a milliliter) or even less, and consequently may not be visually perceptible when observed with conventional imaging techniques. Low-volume fluid accumulations attributable to inflammation or immune-endocrine-metabolic tissue injury can result in a fluid pressure increase within a bone on a scale of several millimeters of water (mm $H_2O$) down to several pascals (tenths of a millimeter of water), and therefore can be difficult to detect, for example, by differential pressure sensing. Even so, such low differential pressures within enclosed bone space may cause pain at a level sufficient to be sensed and cause discomfort in an individual. It is within the scope of this invention to perform decompression of intraosseous pressure on the basis of a clinical observation of pain in a patient that can be attributed to intraosseous pressure but might not be able to be verified through conventional imaging techniques, and such a capability of addressing this pathophysiology opens a new path in treatment of painful conditions that may be chronic and poorly-identifiable.

Figure 3:
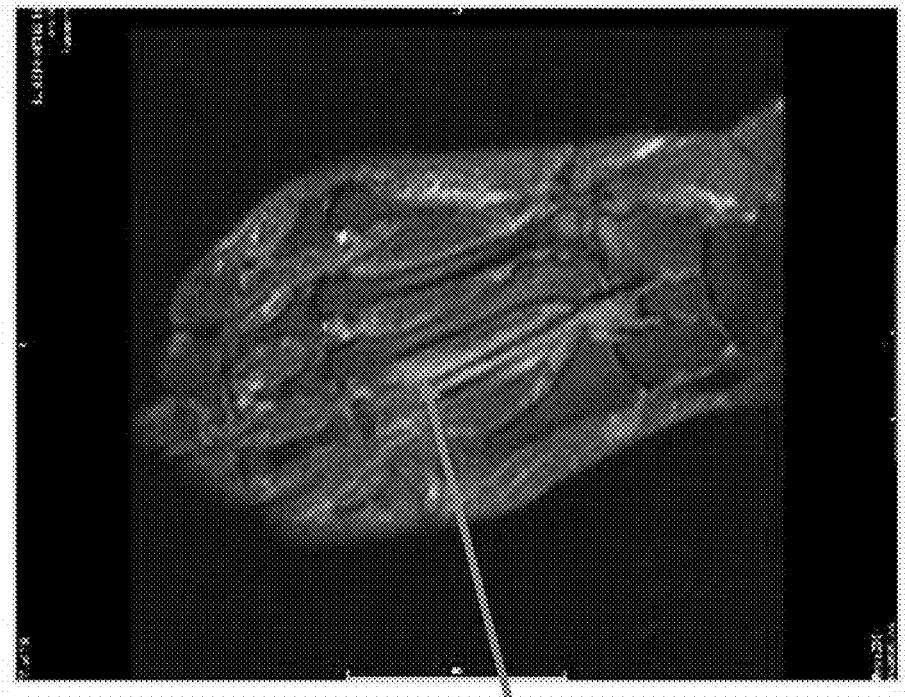
FIG. 3 shows an X-ray image along the long axis of the second metatarsal bone of the left foot of a patient, and indicates a locality where bone edema is present.
Figure 4:
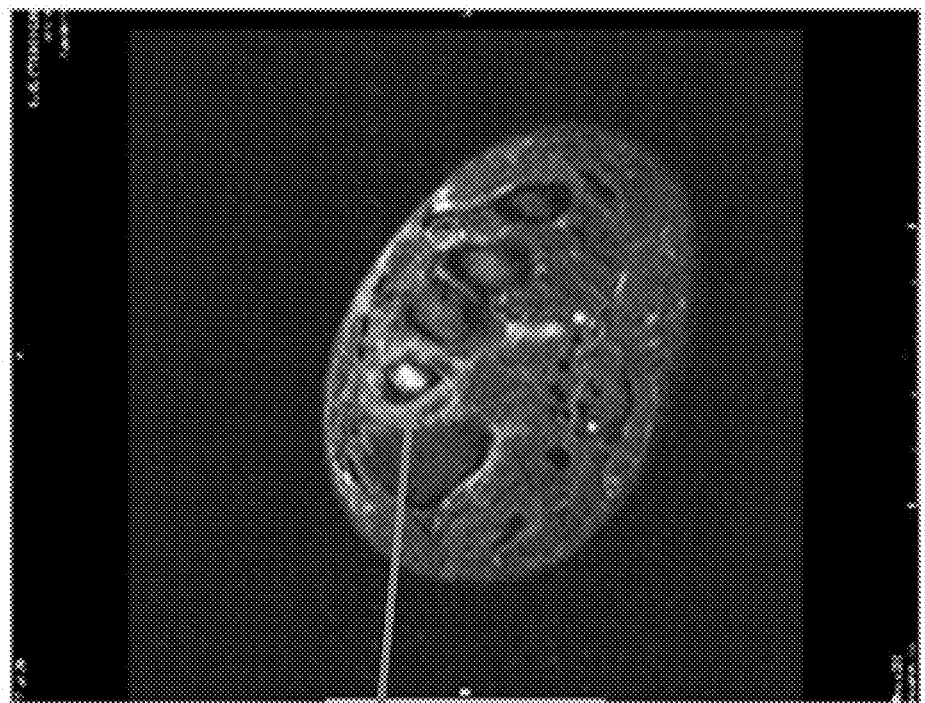
FIG. 4 shows an X-ray image along the short axis of the second metatarsal bone of FIG. 3, and indicates a locality where bone edema is present.

FIG. 3 shows an X-ray image along the long axis of the second metatarsal bone of the left foot of a human. In FIG. 3, the highly localized white area visible in the image indicates fluid of the type that may accumulate in instances such as, but not limited to, inflammation and immune-endocrine-metabolic tissue injury. FIG. 4 shows an image along the short axis of the same bone as FIG. 3. Again, the white area indicates fluid of the type that may accumulate in instances such as, but not limited to, trauma, inflammation, and immune-endocrine-metabolic tissue injury. In comparing FIGS. 3 and 4 to FIGS. 1 and 2, it should be evident that each area indicating fluid accumulation in FIGS. 3 and 4 is significantly smaller and more localized than the fluid accumulation indicated in FIGS. 1 and 2, corresponding to a smaller volume of accumulated fluid. Whereas fluid is visible within the images of FIGS. 1 through 4, pain can be attributed to a fluid that is present within a bony structure in such a small amount and/or in the form of a vapor (gas) that would not be visible in FIGS. 1 through 4. For purposes of this disclosure, a small volume of accumulated fluid (e.g., less than a milliliter) present as a result of edema associated with a physiological condition is termed a Small Magnitude Intraosseous Fluid (SMIF), particularly if its likely cause is (though is not limited to) trauma, inflammation and immune-endocrine-metabolic tissue injury. Differential intraosseous pressures associated with SMIF may be on the order of several millimeters of water and can sometimes be as low as a few pascals, and therefore may be referred to herein as small magnitude changes in intraosseous pressure.

This disclosure describes techniques and methods capable of reducing or possibly eliminating SMIF that may contribute to small magnitude changes in intraosseous pressure, which in turn can cause pain in an individual. In this disclosure, this technique will be called "SMIF decompression" and performed with the intent to reduce bone pain by eliminating (or at least substantially reducing) SMIF thereby reducing intraosseous pressure to more tolerable levels. As noted above, SMIF decompression may be performed on the basis of a clinical observation of pain in a patient that a healthcare professional believes to be attributable to intraosseous pressure, yet is unable to verify through conventional imaging techniques.

FIGS. 5 through 7 schematically represent perspective, top, and side views of a pilot (guide) 10 of this disclosure that can serve as a guide to introduce needles, drill bits, and other tools capable of penetration into a bone (hereinafter, "penetration tool" or "penetration tools"). As represented in the nonlimiting embodiment of FIGS. 5 through 7, the pilot 10 has a circular cross-section along its entire length, including at first and second ends 12 and 14 thereof, though other cross-sections are possible. The pilot 10 has a tubular shape that defines openings 16 and 18 at its first and second ends 12 and 14, respectively. The first opening 16 at the first end 16 and an internal passage 20 that extends from the first opening 16 to the opening 18 at the second end 14 of the pilot 10 are capable of accepting a penetration tool (not shown) inserted through the first opening 16. The pilot 10 of FIGS. 5 through 7 has an external bevel 22 on the circumference at its second end 16 to facilitate partial insertion of the pilot 10 in a hole drilled into a bone so that a substantially liquid-tight seal can be achieved between the pilot 10 and bone.

Prior to using the pilot 10 to perform SMIF decompression, skin overlying an effected bone (in which intraosseous pressure is present) is sterilized. Thereafter, a penetration tool, for example a needle, is inserted into the internal passage 20 of the pilot 10 to protrude through its second opening 18, and thereafter the penetration tool and pilot 10 are together caused to penetrate through any soft tissue between the skin and bone until the bone is encountered. The penetration tool may be used to administer a local anesthesia while the tool penetrates the skin and soft tissue. This technique of anesthesia is known and routine to those skilled in the art.

Figure 8:
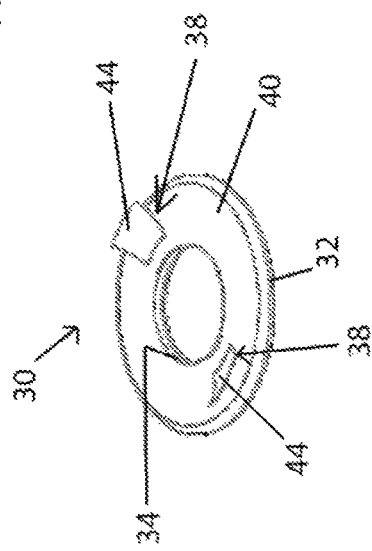
FIGS. 8 through 10 schematically represent, respectively, perspective, top, and side views of an anchor capable of use in a nonlimiting pain treatment method of this disclosure.
Figure 9:
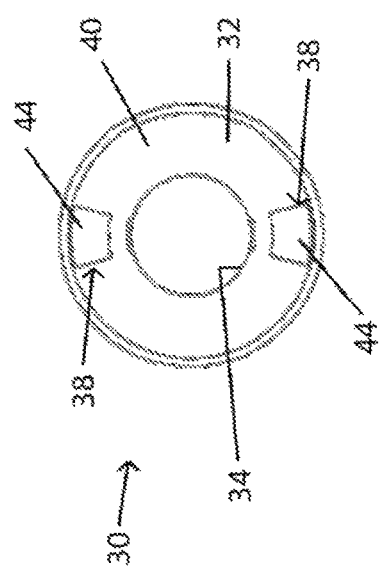
Figure 10:
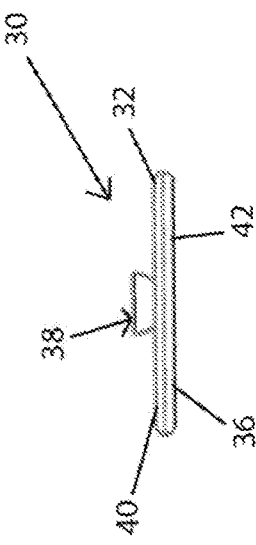

The pilot 10 has a length sufficient to extend through the soft tissue to the surface of the bone, while the first end 12 and first opening 16 of the pilot 10 remain exposed outside the skin. The penetration tool is then removed from the pilot 10 through its exposed first opening 16, after which an anchor 30 schematically shown in FIGS. 8 through 10 is placed over the first end 12 of the pilot 10 so that the anchor 30 contacts the skin. As seen in FIGS. 8 through 10, the anchor 30 has a base 32 in which a central opening 34 is defined. The opening 34 has an appropriate shape and is of sufficient size so that the first end 12 of the pilot 10 is able to pass through the opening 34 during installation of the anchor 30. The base 32 of the anchor 30 has a lower surface 36 that faces and contacts the skin, and flaps 38 protrude from an oppositely-disposed upper surface 40 of the base 32. The base 32 of the anchor 30 has a protective cover 42 for temporarily covering an adhesive on its lower surface 32, such that removal of the cover 42 enables the lower surface 36 of the anchor 30 to adhere to the skin. Similarly, the protective covers 44 temporarily cover an adhesive on the flaps 38, such that removal of the covers 44 enables the flaps 38 to adhere to the outer surface of the pilot 10, for example, at a tapered region 24 of the pilot 10 joining its first end 12 to a smaller-diameter midregion 26 of the pilot 10. In this manner, the pilot 10 can be secured to the surface of the skin. A nonlimiting example of a suitable material for the anchor 30 is a thick paper material.

Figure 18:
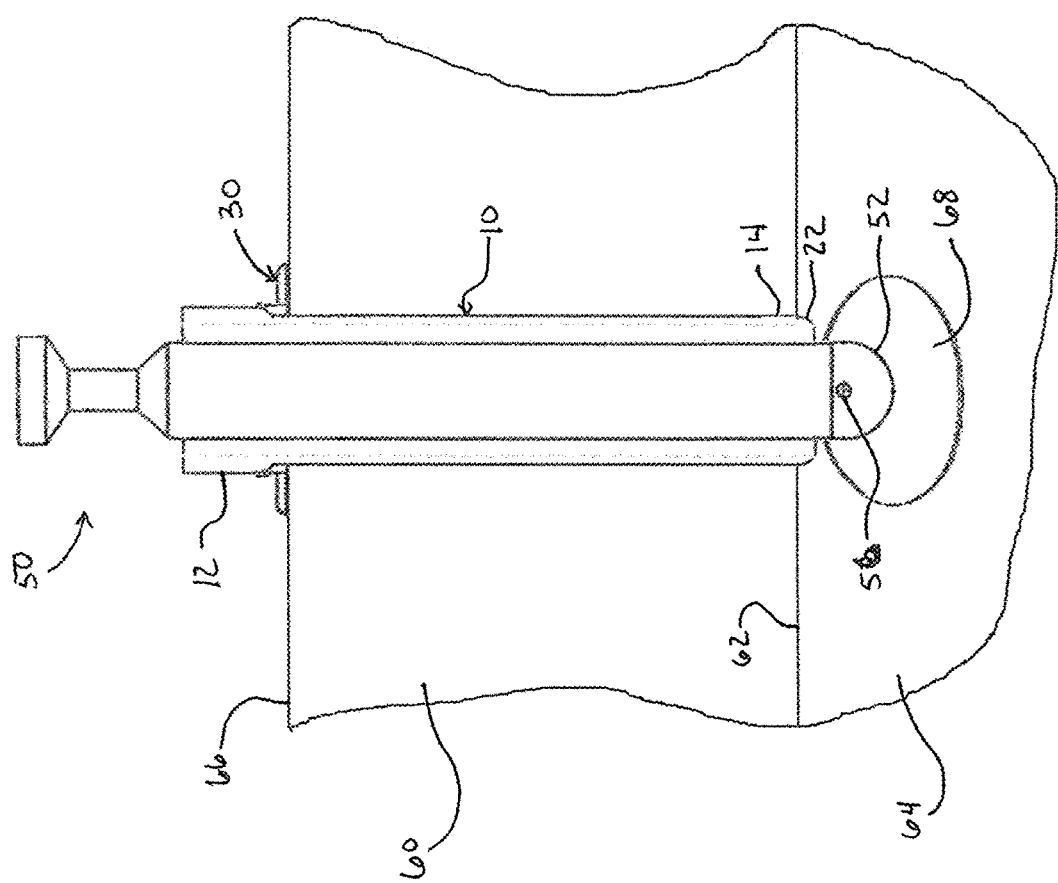
FIG. 18 schematically represents the pilot of FIGS. 5 through 7, the anchor of FIGS. 8 through 10, and the drill bit of FIGS. 11 through 13 assembled and extending through soft tissue to the surface of a bone in accordance with a nonlimiting procedural step that can be performed during a method of this disclosure.

Following securement of the pilot 10 with the anchor 30, another penetration tool may then be inserted into the internal passage 20 of the pilot 10 through its first opening 16 for the purpose of drilling through the bone and into its cortex. FIGS. 11 through 13 schematically represent a drill bit 50 as a nonlimiting example of a suitable penetration tool, and FIGS. 14 through 17 schematically represent an instrument 70 that includes the pilot 10 of FIGS. 5 through 7, the anchor 30 of FIGS. 8 through 10 assembled on the pilot 10, and a cutting face 52 of the drill bit 50 of FIGS. 11 through 13 protruding through the second opening 18 of the pilot 10. As schematically represented in FIG. 18, with the pilot 10 extending through soft tissue 60 to the surface 62 of a bone 64, and with the first end 12 of the pilot 10 exposed above the skin 66, drilling continues until the bevel 22 at the second end 14 of the pilot 10 engages and seals the opening formed by the drill bit 50 at the surface 62 of the bone 64. The distance required to be drilled is dependent on the location and size of the bone 64 and the location and volume of fluid 68 that has accumulated within the bone 64, which in turn will be dependent on the location of the pain in the individual. To prevent bone necrosis due to heat generated by drilling, irrigation with an irrigation fluid (a non-limiting example of which is sterile water) may be introduced through the drill bit 50. For this purpose, FIGS. 11 through 13 depict an irrigation entry port 54 located at one end of the bit 50 opposite its cutting face 52, and FIGS. 11 through 13 and 18 depict an irrigation exit port 56 located adjacent the cutting face 52 of the bit 50. The irrigation fluid can be delivered to the drill bit 50 through an irrigation port 72 on the instrument 70 seen in FIGS. 14 through 17. The liquid-tight seal formed between the bevel 22 of the pilot 10 and the surface 62 of the bone 64 enables the irrigation fluid and bone debris generated by the drilling process to be removed through the internal passage 20 of the pilot 10 using any suitable means, for example, using a suction tube 74 seen in FIG. 17. After the bone cortex is penetrated, the drill bit 50 can be removed and a low-grade suction performed through the internal passage 20 of the pilot 10 to remove the fluid 68 from the bone, i.e., the fluid (liquid or vapor) causing the edema that is the source of pain, to perform what has been defined herein as SMIF decompression. After removing the fluid 68, the pilot 10 (along with the anchor 30) can be removed and conventional dressing applied to the surgical entry wound created by the pilot 10.

The entire procedure described above can be done under fluoroscopic guidance. The optimal vacuum level and duration for removing the fluid from the bone will depend on the anatomical location of the suspected intraosseous edema and can be experimentally defined through clinical studies. Furthermore, optimal shapes, sizes, diameters, and lengths of the pilot 10 and penetration tool (e.g., the drill bit 50, needles, etc.) will vary depending on the location of the bony structure, and as such, it is expected that an assortment of pilots 10 and penetration tools would be made available.

Figure 19:
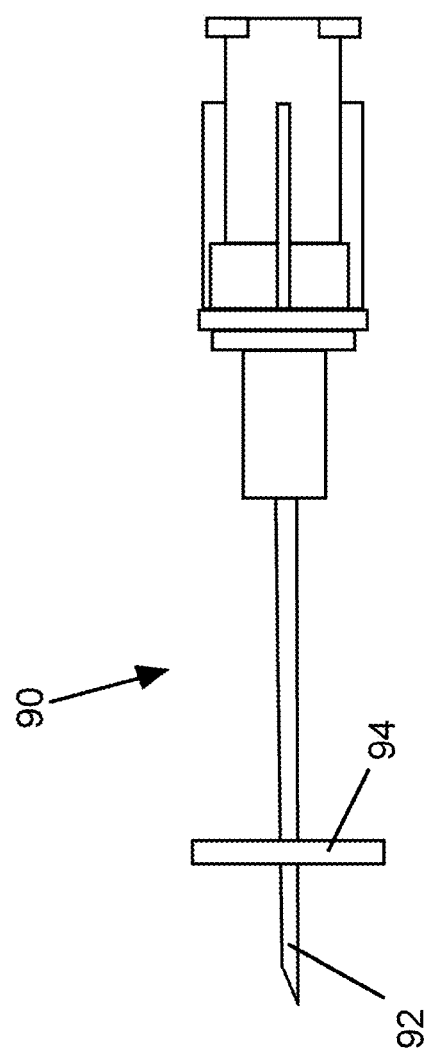
FIG. 19 is a partial view of an instrument capable of use in another nonlimiting pain treatment method of this disclosure.

It should be recognized that in adopting the methods described in this disclosure, bones close to the skin (for example. skull, sternum, olecranon, iliac, etc.) may be accessed and penetrated with a strong needle without need for drilling, in which case suction can be applied directly to the needle. This situation is illustrated in FIG. 19, which is a partial view of an embodiment of an instrument 90 that can be used if a separate drilling operation is not needed to access a bone. The instrument 90 comprises a needle 92 of sufficient strength to penetrate bone (as known in the art). The needle 92 is equipped with a stopper bar 94 mounted a predetermined distance from its point to limit the distance that the needle 92 is able to penetrate into the targeted bone. Properly locating the stopper bar 94 on the needle 92 can ensure that the needle 92 will not penetrate too deeply into or through the bone. For example, the stopper bar 94 can be specifically located on the needle 92 in FIG. 19 to penetrate the periosteum of a bone. The instrument 90 can be manufactured to have a needle 92 of whatever size and length is appropriate for a given procedure, and with a stopper bar 94 appropriately located a distance from the needle tip to access essentially any bone, based on the depth of the bone beneath the skin.

Figure 20:
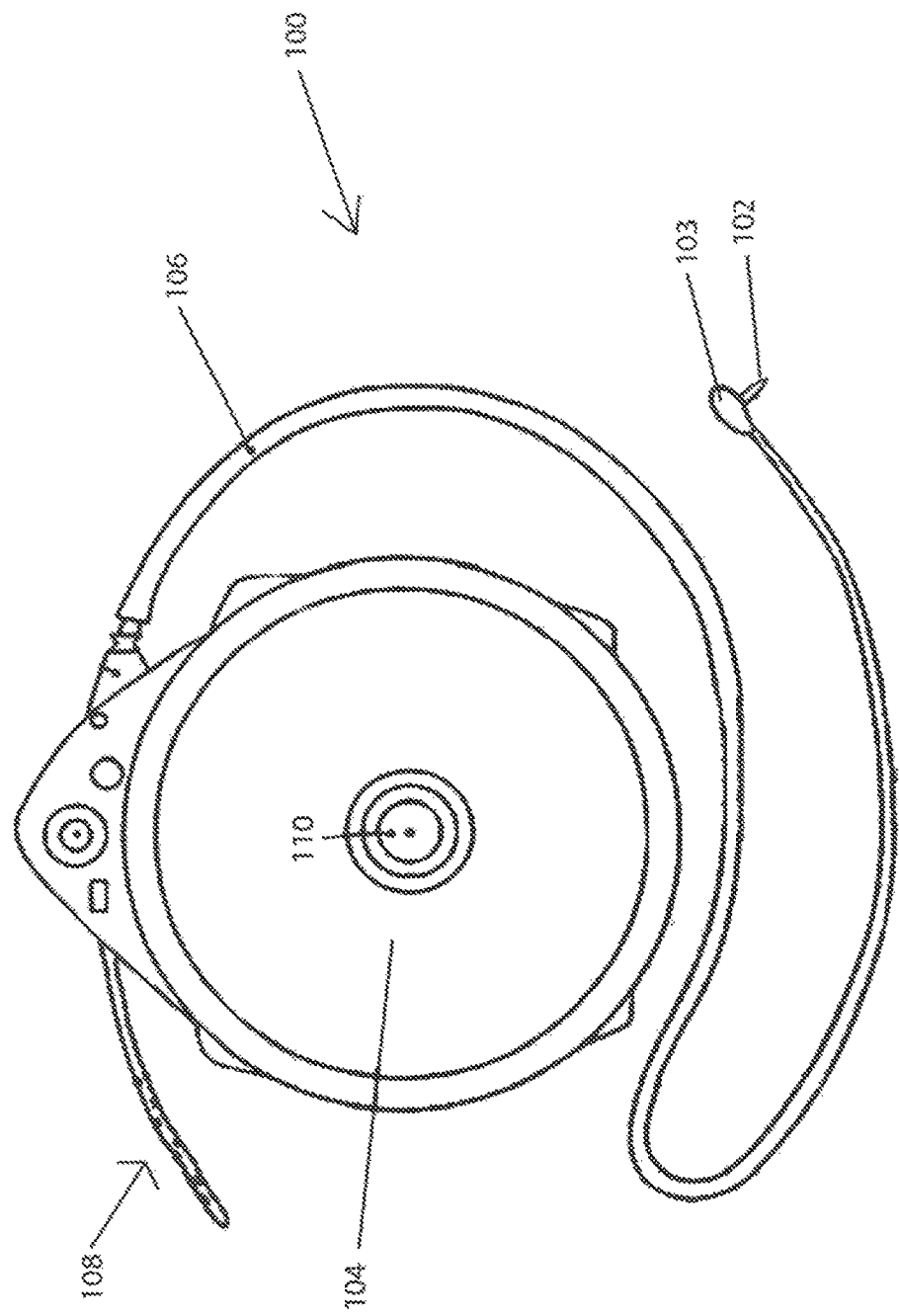
FIG. 20 schematically represents an embodiment of an instrument capable of use in another nonlimiting pain treatment method of this disclosure.

FIG. 20 shows another variation of an instrument 100 of this disclosure intended to remove fluid from bones that are located relatively deep within a living body and suffer recurrent intraosseous edema. In FIG. 20, an indwelling needle 102 coupled to a housing 103, which in turn is fluidically connected to an implantable reservoir 104 through an implantable pump catheter 106. At least the needle 102 and optionally the housing 103 and pump catheter 106 are sized and configured to be placed in a predrilled hole in a bone, which may be formed in a manner as was previously described in prior embodiments. In the embodiment of FIG. 20, the indwelling needle 102 is implanted in the bone, and the pump catheter 106 draws fluid from the bone through the needle 102 and then dispenses the drawn fluid directly into soft tissue via a dispensing catheter 108. Alternatively, the drawn fluid may be accumulated in the reservoir 104 and later drained from the reservoir 104 through an extraction port 110 or periodically emptied with a needle (not shown) that can be inserted into the reservoir 104.

While the disclosure has been described in terms of specific embodiments, it is apparent that other forms could be adopted by one skilled in the art. For example, the pilot 10, instrument 70, and penetration tools (for example, the drill bit 50) could differ in appearance and construction from the embodiments described herein and shown in the drawings, various materials could be used in the fabrication of the pilot 10, instrument 70, and penetration tools, and under standard conditions the procedure described above could be performed by a robot. In addition, the invention encompasses additional or alternative embodiments in which one or more features or aspects of a particular embodiment could be eliminated or two or more features or aspects of different disclosed embodiments could be combined. Accordingly, it should be understood that the invention is not limited to any embodiment described herein or illustrated in the drawings. It should also be understood that the phraseology and terminology employed above are for the purpose of describing the disclosed embodiments and investigations, and do not necessarily serve as limitations to the scope of the invention. Therefore, the scope of the invention is to be limited only by the following claims.

The invention claimed is:

1. A method of treating pain through decompression of a fluid within a bone of a living being, the method comprising:
   identifying the bone of the living being as associated with pain;
   using one or more tools to penetrate soft tissue between the bone and the skin of the living being, penetrate the bone of the living being, penetrate into the cortex of the bone, and form a seal against a surface of the bone; and
   removing the fluid from within the bone, wherein the fluid comprises a vapor.

2. The method of claim 1, wherein the fluid further comprises a liquid.

3. The method of claim 1, wherein the volume of the fluid is less than a milliliter.

4. The method of claim 1, wherein the one or more tools comprise an instrument that penetrates the soft tissue, the bone, and the cortex of the bone, forms the seal against the surface of the bone, and removes the fluid from within the bone, the instrument comprising:
   a pilot adapted to penetrate the soft tissue between the bone and the skin of the living being, the pilot having a first opening at a first end thereof, a second opening at an oppositely-disposed second end thereof, an internal passage therebetween adapted for guiding a penetration tool, and a bevel at the second end, the bevel circumscribing the second opening and being configured to seal against a surface of the bone;
   an anchor adapted for securing the pilot to the skin after the second end of the pilot has penetrated the skin and soft tissue;
   at least one penetration means sized to be inserted into the internal passage of the pilot and protrude through the second opening of the pilot;
   irrigation means for removing an irrigation fluid and bone debris created by penetrating the bone with the penetration means; and
   suction means for removing the fluid from within the bone.

5. The method of claim 4, wherein the anchor comprises a base, a central opening in the base sized to accommodate the pilot therethrough, an adhesive on a first surface of the base for temporarily adhering the anchor to the skin, and an adhesive on a second surface of the base for temporarily adhering the anchor to the pilot.

6. The method of claim 5, wherein the anchor further comprises at least one flap that protrudes from the base and defines the second surface thereof.

7. The method of claim 4, wherein the penetration means is a drill bit or a needle.

8. The method of claim 4, wherein the irrigation means comprises a port in the penetration means.

9. The method of claim 4, wherein the suction means comprises an implantable pump catheter connected to the penetration means and adapted to dispense the fluid directly into tissue of the living being or dispense the fluid outside of the living being.

10. The method of claim 4, wherein the pilot is secured to the skin with an anchor comprising a base and a central opening in the base, the method comprising:
    assembling the anchor to the pilot so that the first end of the pilot passes through the central opening of the anchor;
    temporarily adhering the anchor to the skin; and
    temporarily adhering the anchor to the pilot.

11. The method of claim 1, further comprising using an irrigation system to remove bone debris generated during the penetration of the bone.

12. The method of claim 1, wherein one of the one or more tools is
    a needle with a stopper bar to limit penetration to the periosteum of the bone.

13. The method of claim 1, further comprising
    accumulating the fluid removed from the bone in an implanted reservoir; and then
    either dispensing the accumulated fluid directly into soft tissue within the living being or outside of the living being.

14. The method of claim 13, wherein the accumulated fluid is dispensed directly into the soft tissue within the living being.

15. The method of claim 14, further comprising implanting a reservoir and a dispensing catheter in the living being, and the accumulated fluid is accumulated in the reservoir and then dispensed directly into the soft tissue with the dispensing catheter.

16. The method of claim 13, wherein the accumulated fluid is dispensed outside of the living being.

17. The method of claim 16, further comprising implanting a reservoir in the living being and accumulating the accumulated fluid in the reservoir.

18. The method of claim 17, further comprising draining the accumulated fluid from the reservoir through an extraction port of the reservoir.

19. The method of claim 17, further comprising draining the accumulated fluid from the reservoir with a needle inserted into the reservoir.

* * * * *